United States Patent [19]

Didier et al.

[11] Patent Number: 4,461,289
[45] Date of Patent: Jul. 24, 1984

[54] SOLE INCORPORABLE INTO PLASTER CAST BANDAGES FOR THE FOOT

[76] Inventors: Philippe Didier, Rue Gustave Deleris, Bulgneville - 88140 Contrex; Francis Vermonet, 1 Rue Kennedy, Neufchateau 88300, both of France

[21] Appl. No.: 369,635

[22] Filed: Apr. 19, 1982

[30] Foreign Application Priority Data

Apr. 28, 1981 [FR] France ............................. 81 08437

[51] Int. Cl.$^3$ ................................................ A61F 5/01
[52] U.S. Cl. .................................................... 128/83.5
[58] Field of Search ............................... 128/83, 83.5

[56] References Cited

U.S. PATENT DOCUMENTS

| | | | |
|---|---|---|---|
| 2,875,752 | 3/1959 | Lovich | 128/83 |
| 3,068,861 | 12/1972 | Hoopes | 128/83.5 |
| 3,307,536 | 3/1967 | Blosser | 128/83.5 |
| 3,613,674 | 10/1971 | Volz | 128/83.5 |
| 3,680,550 | 8/1972 | Tunstall | 128/83.5 |
| 3,916,538 | 11/1974 | Loseff | 128/83.5 X |

FOREIGN PATENT DOCUMENTS 2328449  5/1977  France .

Primary Examiner—John D. Yasko
Attorney, Agent, or Firm—Young & Thompson

[57] ABSTRACT

A sole incorporable into plaster cast bandages for the foot, comprising a body 1 of rigid material corresponding substantially to a human foot size and shape. Under the lower surface of the sole are provided three transverse bearing surfaces 2 protruding from the lower surface by at least the current thickness of a walking plaster cast. The plastered bands which form the bandage are put into position around the foot under the sole by passing on either side of and between the downwardly protruding bearing surfaces. A rear lug 4 is provided, having a length substantially equal to the projection of the transverse bands and extending obliquely and toward the outside from the outer lateral edge of the rear portion of the sole heel.

2 Claims, 4 Drawing Figures

SOLE INCORPORABLE INTO PLASTER CAST BANDAGES FOR THE FOOT

FIELD OF THE INVENTION

The present invention relates to foot bandages made of plastered bands and called walking plaster casts, either of the type of the plastered boot extending to below the knee or of the so-called cruro-pedal type extending up to the thigh.

BACKGROUND OF THE INVENTION

With walking plaster casts, the plaster cast has to be protected from a direct contact with the ground since otherwise a fracture and a disintegration of at least part of the plastered mass would rapidly occur. The technique known hitherto consists in incorporating into the plaster mass which is below the foot, wads or pads protruding below the plaster cast and called "walking heel-pieces". Said walking heel-pieces comprise a body of generally cylindrical shape the upper end of which is formed with flexible side ears or bands imbedded when laying the plaster cast inside the layers of plastered bands. With such walking heel-pieces, the body weight is transferred to the ground via the section of the cylindrical body, and due to the small thickness of the plastered mass interposed between the foot and the upper surface of the heel-piece on the one hand, and to the residual flexibility resulting therefrom of the interposed plastered layer on the other hand, the result is a notable compression of the area of the sole of the foot situated above the heel-piece, which causes a feeling of discomfort and even of pain. Moreover, when the patient is in a seated position with his leg stretched, the heel-piece is no longer in contact with the ground and the portion of the plaster cast which is behind the heel is in contact with the ground.

OBJECTS AND SUMMARY OF THE INVENTION

The present invention has for its object to remedy these drawbacks of known walking heel-pieces and it relates to a sole made of a rigid material corresponding substantially to the patient's foot size and comprising, at least under the lower surface of the sole, at least one bearing surface protruding with respect to said lower surface by at least the current thickness of a walking plaster cast.

When laying the walking plaster cast, the sole is applied directly against the sole of the foot and maintained in place by plastered bands which are passed under the sole on either side of the protruding portion forming the bearing surface.

According to a preferred embodiment, the sole comprises several bearing surfaces formed by protruding transverse bands, the plastered bands being engageable in the space between two contiguous transverse bands. Preferably and in order to facilitate walking with the plaster cast, the foremost protruding transverse band is situated in the widest metatarsal region of the sole and the rearmost band in the anterior portion of the heel. Preferably, the anterior portion of the lower surface of the sole in front of the forward transverse band is raised.

According to a preferred embodiment, the sole comprises three protruding transverse bands.

In order to avoid, in a seated position with the leg stretched, the contact of the plaster cast with the ground, the sole is formed with a rear lug having a length substantially equal to the protrusion of the transverse bands and extending obliquely and toward the outside from the outer lateral edge of the rear portion of the sole heel.

Moreover, said lug on either side of which pass the plastered bands, facilitates the laying of the plaster cast and the maintenance in position of the bands until complete setting.

In order to improve the comfort, the sole upper surface comprises a support for the arch of the foot and/or a metatarsal wad.

Preferably, the lower surface of the transverse bands is provided with an anti-skid coating.

The sole according to the invention is preferably and according to the most simple mode of manufacture realized in a molded rigid plastics material such as polyurethane. However, it could comprise a body and a removable orthopaedic and cleanliness sole constituting the upper surface of the sole and forming the support for the arch of the foot and the metatarsal wad. Such removable cleanliness sole can be thin and made of a plastic foam.

BRIEF DESCRIPTION OF THE DRAWINGS

The present invention will become more apparent when reading the following detailed description of an embodiment, with reference to the accompanying drawing wherein.

DETAILED DESCRIPTION OF THE EMBODIMENT

Figure 1:
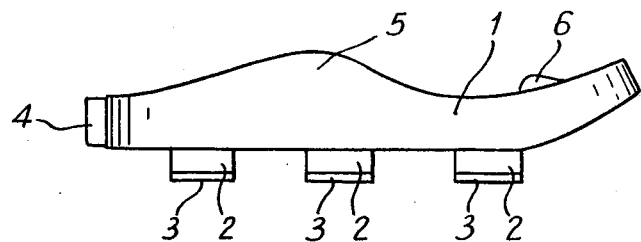
FIG. 1 is a side elevation view of the sole.
Figure 2:
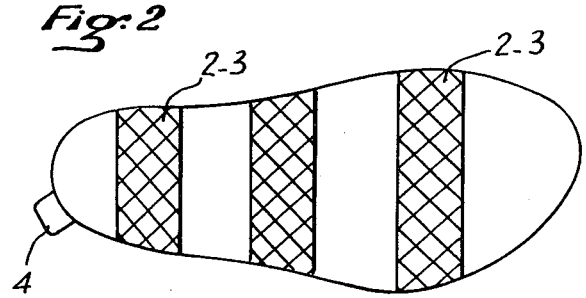
FIG. 2 is a view from below.
Figure 3:
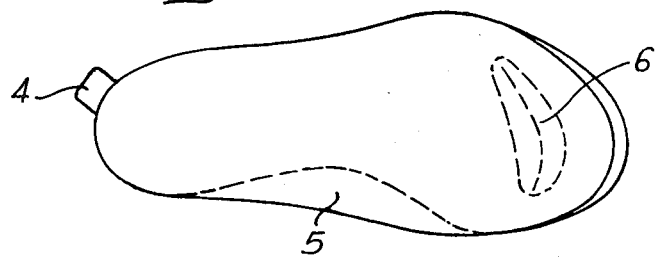
FIG. 3 is a view from above.

The sole according to the invention comprises a body 1 made of molded rigid polyurethane with, under the lower surface of the sole, three protruding bands 2 the lower bearing surface 3 of which is constituted by an anti-skid band. Said bands have an approximate width of 3 centimeters and their spacing is of the same order, their thickness being from 15 to 20 millimeters.

Behind the body, from the outer rear edge of the sole and extending obliquely toward the outside is provided a lug 4 which protrudes by about 20 millimeters with respect to the sole outer edge.

On the sole upper surface are provided a support 5 for the arch of the foot and a metatarsal wad 6.

Figure 4:
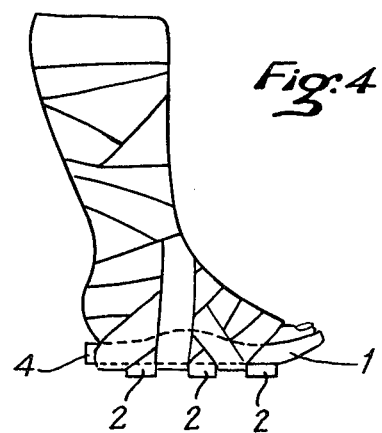
FIG. 4 is a schematic side elevation view of a plastered boot using the sole.

As is shown in FIG. 4, the foot bears directly on the sole and the plastered bands are wound in the usual way by passing under the sole between the transverse bands 2 and at the rear between the rear edge of the transverse band and the sides of the lug 4.

We claim:

1. A sole for providing a plaster cast bandage for the foot, comprising a body made of a rigid material whose upper surface corresponds substantially to a human foot shape and size and whose lower surface comprises at least one bearing surface constituted by at least one protruding transverse band, said sole being formed with a rear lug having a length substantially equal to the projection of said at least one transverse band and extending obliquely and toward the outside from the outer lateral edge of the rear portion of the sole heel.

2. A foot plastered bandage including a sole as claimed in claim 1, and a plastered band extending under the sole between said at least one protruding transverse band and said rear lug.

* * * * *